United States Patent
Kim et al.

(10) Patent No.: US 9,394,546 B2
(45) Date of Patent: Jul. 19, 2016

(54) RECOMBINANT YEAST TRANSFORMANT AND PROCESS FOR PREPARING IMMUNOGLOBULIN FC FRAGMENT EMPLOYING THE SAME

(71) Applicant: HANMI PHARM. CO., LTD., Hwaseong-si, Gyeonggi-do (KR)

(72) Inventors: Jin-Sun Kim, Yongin-si (KR); Yong Ho Huh, Seoul (KR); Euh Lim Oh, Hanam-si (KR); Min Young Kim, Anseong-si (KR); Sung Youb Jung, Suwon-si (KR); Se Chang Kwon, Seoul (KR)

(73) Assignee: HANMI PHARM. CO., LTD, Hwaseong-si (KR)

( * ) Notice: Subject to any disclaimer, the term of this patent is extended or adjusted under 35 U.S.C. 154(b) by 0 days.

(21) Appl. No.: 14/763,722

(22) PCT Filed: Feb. 3, 2014

(86) PCT No.: PCT/KR2014/000901
§ 371 (c)(1),
(2) Date: Jul. 27, 2015

(87) PCT Pub. No.: WO2014/119956
PCT Pub. Date: Aug. 7, 2014

(65) Prior Publication Data
US 2015/0361437 A1    Dec. 17, 2015

(30) Foreign Application Priority Data
Jan. 31, 2013 (KR) .................. 10-2013-0011471

(51) Int. Cl.
*C12N 1/15* (2006.01)
*C12P 21/04* (2006.01)
*C12N 15/81* (2006.01)
*C07K 16/00* (2006.01)

(52) U.S. Cl.
CPC .............. *C12N 15/815* (2013.01); *C07K 16/00* (2013.01); *C12N 15/81* (2013.01); *C07K 2317/14* (2013.01); *C07K 2317/52* (2013.01)

(58) Field of Classification Search
None
See application file for complete search history.

(56) References Cited

U.S. PATENT DOCUMENTS

| 6,660,843 | B1 | 12/2003 | Feige et al. |
| 2004/0044188 | A1 | 3/2004 | Feige et al. |
| 2004/0053845 | A1 | 3/2004 | Feige et al. |
| 2010/0092464 | A1 | 4/2010 | Kavanaugh et al. |
| 2011/0201053 | A1 | 8/2011 | Gion et al. |
| 2015/0361437 | A1* | 12/2015 | Kim ...................... C12N 15/81 530/387.1 |

FOREIGN PATENT DOCUMENTS

| KR | 10-2005-0047030 A | 5/2005 |
| KR | 10-0798894 B1 | 1/2008 |
| KR | 10-2009-0038260 A | 4/2009 |

OTHER PUBLICATIONS

Song Lin et al., "Selection of Pichia pastoris strains expressing recombinant immunoglobin G by cell surface labeling", Journal of Immunological Methods, 2010, pp. 66-74, vol. 358.
Thomas I. Potgieter et al., "Production of monoclonal antibodies by glycoengineered Pichia pastoris", Journal of Biotechnology, 2009, pp. 318-325, vol. 139.
International Searching Authority, International Search Report of PCT/KR2014/000901 dated May 28, 2014 [PCT/ISA/210].
International Searching Authority, Written Opinion of PCT/KR2014/000901 dated May 28, 2014 [PCT/ISA/237].

\* cited by examiner

*Primary Examiner* — Michael Burkhart
(74) *Attorney, Agent, or Firm* — Sughrue Mion, PLLC

(57) ABSTRACT

The present invention relates to a transformant prepared by introducing an expression vector comprising a polynucleotide encoding for a human immunoglobulin Fc fragment into *Pichia* sp. yeast, a method for producing an immunoglobulin Fc fragment comprising culturing the transformant, and recovering the immunoglobulin Fc fragment from the culture, and an immunoglobulin Fc fragment, prepared by the above method for use as a drug carrier. The transformant is suggested as a solution to the problems associated with the use of *E. coli* or animal cells as hosts for producing immunoglobulin Fc fragments useful as drug carriers, so that it can find various applications in the effective and economical production of drugs.

13 Claims, 3 Drawing Sheets

US 9,394,546 B2

RECOMBINANT YEAST TRANSFORMANT AND PROCESS FOR PREPARING IMMUNOGLOBULIN FC FRAGMENT EMPLOYING THE SAME

CROSS REFERENCE TO RELATED APPLICATIONS

This application is a National Stage of International Application No. PCT/KR2014/000901, filed Feb. 3, 2014, claiming priority based on Korean Patent Application No. 10-2013-0011471, filed Jan. 31, 2013, the contents of all of which are incorporated herein by reference in their entirety.

TECHNICAL FIELD

The present invention relates to a recombinant yeast transformant, and a process for preparing an immunoglobulin Fc fragment using the same. More particularly, the present invention relates to a transformant prepared by introducing an expression vector comprising a polynucleotide coding for a human immunoglobulin Fc fragment into Pichia sp. yeast, a method for producing an immunoglobulin Fc fragment, comprising culturing the transformant and recovering the immunoglobulin Fc fragment from the culture, and an immunoglobulin Fc fragment, prepared by the above method for use as a drug carrier.

BACKGROUND ART

With the advance of bioengineering and biotechnology, many bioactive polypeptides (proteins) and peptide medicines have been developed as therapeutic options for various diseases. Due to their low stability, however, such polypeptides or peptide medicines readily denature and thus are highly prone to renal or hepatic clearance. Accordingly, protein medicines comprising polypeptides as medicinally active ingredients suffer from the disadvantage of frequent necessary administration to patients to maintain appropriate serum levels and titers thereof. It is thus essential for the development of protein medicines that allow for them to be maintained at a proper level in the body without frequent administration.

To solve these problems, a lot of effort has been devoted to improving the serum stability of protein drugs and maintaining high drug concentration level in blood for a prolonged period of time for the maximization of the pharmaceutical efficacy of the drugs, thus improving change of protein formulations, fusion with other proteins or binding polymer have been attempted. One of the most favored methods has been focused on the fusion of immunoglobulins to proteins in recent years.

There have been many attempts made to increase the stability of protein medicines by use of immunoglobulins and their fragments, as described in U.S. Pat. No. 5,045,312 wherein human growth hormone is conjugated to bovine serum albumin or mouse immunoglobulin via a cross-linking agent. The conjugates have enhanced activity compared with unmodified growth hormone. Other various fusion proteins are also prepared as expressed in mammals after the Fc fragment of immunoglobulin is linked to interferon (Korean Patent Publication No. 10-2003-0009464), interleukin-4 receptor, interleukin-7 receptor or erythropoietin (Korean Patent Publication No. 10-249572). PCT Patent Publication No. WO 01/03737 discloses a fusion protein in which a cytokine or a growth factor is linked through an oligopeptide linker to an Fc fragment of immunoglobulin. Also, U.S. Pat. No. 5,116,964 describes a protein which is fused to the amino or carboxy end of an immunoglobulin Fc fragment using a genetic recombination technique. U.S. Pat. No. 5,349,053 discloses a fusion protein in which IL-2 is linked to an immunoglobulin Fc fragment via a peptide linkage.

Many other Fc fusion proteins constructed using genetic recombination techniques have been disclosed, examples of which include a fusion protein of an immunoglobulin Fc fragment with interferon-beta or a derivative thereof (PCT Patent Publication No. WO 00/23472), and an immunoglobulin Fc fragment with an IL-5 receptor (U.S. Pat. No. 5,712,121). Further, an immunoglobulin Fc fragment has been used as a carrier rather than a fusion partner, as disclosed in U.S. Pat. No. 7,736,653.

Production of immunoglobulins or immunoglobulin Fc fragments has been carried out predominantly in E. coli. The American company Amgen Inc. described, in U.S. Pat. No. 6,660,843 and U.S. Pat. Publication Nos. 2004-0044188 and 2004-0053845, a human IgG1 Fc derivative having amino acid deletions at the first five amino acid residues of the hinge region, which is fused to the amino or carboxyl terminal end of a therapeutic protein or a therapeutic protein mimicked by a peptide, and the production thereof using an E. coli host. However, this fusion protein not having a signal sequence is expressed as inclusion bodies, and thus must be subjected to an additional refolding process. This protein refolding process reduces yields, and, especially in a protein present as a homodimer or a heterodimer, remarkably reduces dimer production. Also, when a protein not having a signal sequence is expressed in E. coli, a methionine residue is added to the N-terminus of the expression product due to the feature of the protein expression system of E. coli. The aforementioned expression products of Amgen Inc. have an N-terminal methionine residue, which may induce immune responses upon repeated or excessive administration to the body. Also, since these fusion molecules are expressed in a fusion protein form in E. coli by linking a gene encoding a therapeutic protein to an Fc gene they are difficult to express in E. coli, and a therapeutic protein is difficult to produce in E. coli if its expression in E. coli in a fused form results in a significant decrease or loss of activity. Further, since the fusion of two molecules creates a unnaturally-occurring abnormal amino acid sequence at the connection region between two proteins, the fusion protein could potentially be recognized as a foreign matter by the immune system, and thus induce immune responses.

As described above, the use of E. coli is advantageous in that therapeutically effective proteins can be expressed as aglycosylated forms at high yield thanks to the rapid growth rate of E. coli and the accumulated technology of fermentation and bioengineering, but disadvantageous in that the recombinant proteins have methionine as the first amino terminal residue, as opposed to native proteins, and require a complex purification process in consideration of the removal of E. coli-derived pyrogens (endotoxins) and protein refolding.

On the other hand, the use of animal cells advantageously allows for the production of fusion proteins as glycosylated proteins akin to native immunoglobulin forms, but suffers from the disadvantage of having high production cost, and being high prone to contamination with animal-derived viruses or proteins. There is therefore an increasing demand for solutions to the above-mentioned problems. Recommended is a strategy of utilizing yeasts having the advantages of both E. coli and animal cells as host cells.

Representative among the yeast used for protein production is Saccharomyces cerevisiae. In addition to being safe for the human body, the eukaryote *Saccharomyces cerevisiae* is easy to genetically manipulate and to culture on a large scale. Also, various expression systems for the eukaryote have been developed. When producing higher cell-derived proteins, such as human proteins, using a recombinant method, this microorganism moreover provides the proteins with the ability to be secreted outside the cells and be post-translationally modified, such as via glycosylation. In addition, the recombinant protein of the yeast undergoes folding, and disulfide bond formation, glycosylation during secretion signal-driven extracellular secretion, thus evolving to a fully bioactive form. The yeast is also economically beneficial because it does not require cell lysis and protein refolding, which are of low efficiency. What has been shown as a problem with the protein secretion system of *Saccharomyces cerevisiae* is, however, the great variance in secretion rate depending on the kind of human protein. Often, proteins for use as human medicines of high value are difficult to express and secrete in *Saccharomyces cerevisiae* (Korea Patent No. 10-0798894).

DISCLOSURE

Technical Problem

Leading to the present invention, intensive and thorough research into the use of yeast in producing proteins for human medicines, conducted by the present inventors, resulted in the finding that
*Pichia* sp. yeast, a species of methylotrophic yeast, can be used to produce a secretory immunoglobulin Fc fragment, useful as a drug carrier, at a high expression level with neither an additional refolding process, nor N-terminal modification with an additional amino acid, and that the secretary immunoglobulin Fc fragment can be purified using a simple process, with the minimum load of endotoxin or animal-derived foreign pathogens thereto.

Technical Solution

It is an object of the present invention to provide a transformant prepared by introducing an expression vector comprising a polynucleotide encoding for a human immunoglobulin Fc fragment into a *Pichia* sp. yeast.

It is another object of the present invention to provide a method for producing an immunoglobulin Fc fragment, comprising culturing the transformant, and recovering the immunoglobulin Fc fragment from the culture.

It is a further object of the present invention to provide an immunoglobulin Fc fragment, produced by the method, for use as a drug carrier.

Advantageous Effects

The recombinant transformant of the present invention can overcome the problems associated with the use of *E. coli* or animal cells as host cells in producing an immunoglobulin Fc fragment, is useful as a drug carrier, and can find applications in the effective and economical production of drugs.

BEST MODE

Figure 1:
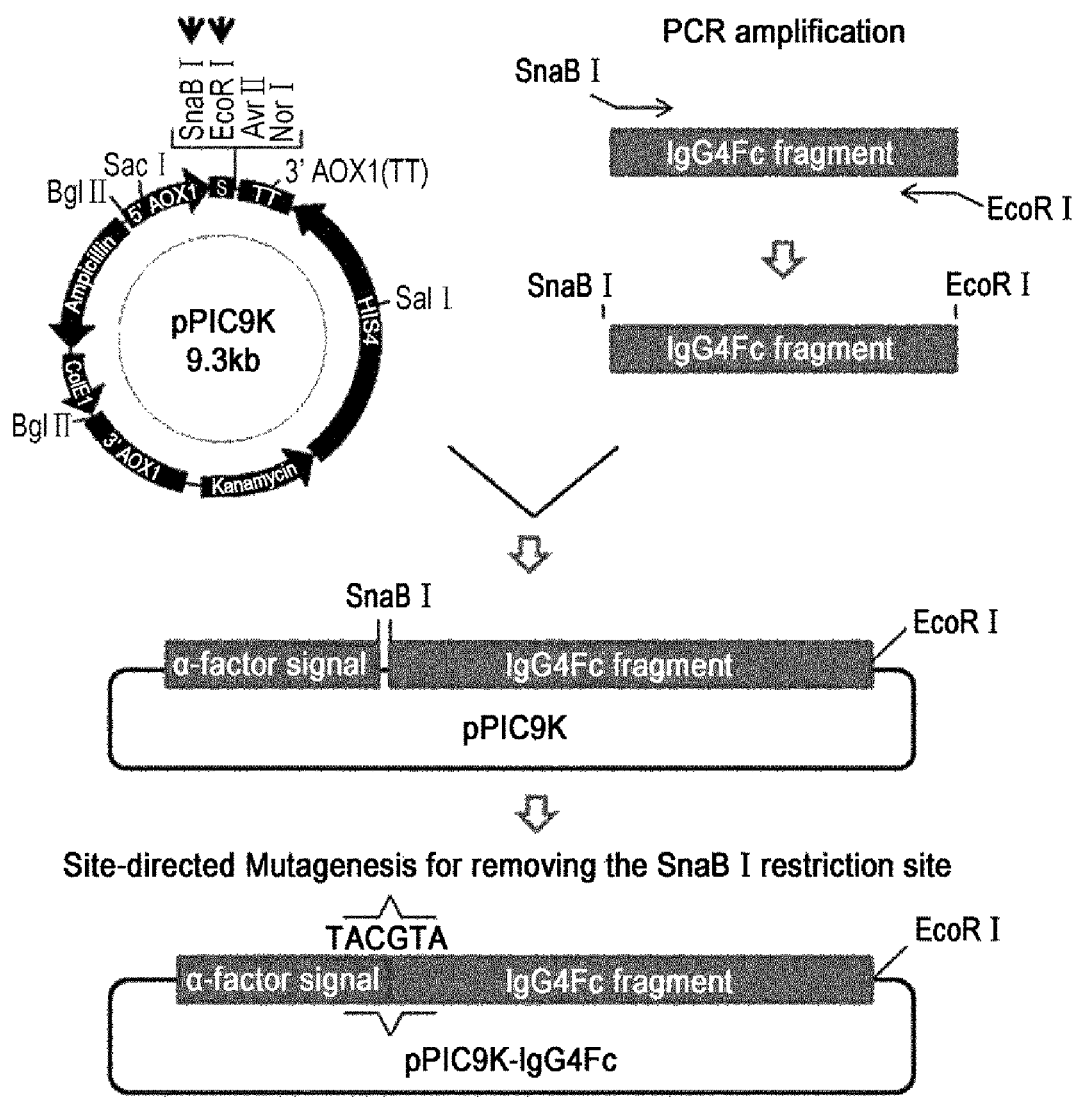
FIG. 1 is a schematic view illustrating processes of constructing the recombinant expression vector pPIC9K-IgG4Fc.

In one embodiment of this aspect, the present invention addresses a transformant, modified by introducing an expression vector comprising a polynucleotide encoding for a human immunoglobulin Fc fragment into *Pichia* sp. yeast, As used herein, the term "immunoglobulin," also known as "antibody," refers to a protein that is produced by the immune system in response to an antigen stimulus and specifically binds to a specific antigen during vigilance through blood and lymph to exert an antigen-antibody reaction. Immunoglobulins are fundamentally composed of two identical full-length light chains and two identical full-length heavy chains, with connections by disulfide bonds between the heavy chains and between the heavy chains and the light chains. There are five distinct types of heavy chains based on differences in the amino acid sequences of their constant regions: gamma ($\gamma$), mu ($\mu$), alpha ($\alpha$), delta ($\delta$) and epsilon ($\epsilon$), and the heavy chains include the following subclasses: gamma 1 ($\gamma$1), gamma 2 ($\gamma$2), gamma 3 ($\gamma$3), gamma 4 ($\gamma$4), alpha 1 ($\alpha$1) and alpha 2 ($\alpha$2). According to the features of the constant regions of the heavy chains, immunoglobulins are classified into five isotypes: IgG, IgA, IgD, IgE and IgM. The representative isotype IgG is further divided into IgG1, IgG2, IgG3 and IgG4 subclasses. For the purpose of the present invention, the term "immunoglobulin" includes a functional fragment of an immunoglobulin molecule as well as a whole immunoglobulin molecule. This functional fragment means a fragment retaining an antigen binding function, and includes Fab, F(ab'), F(ab')2, Fv, scFv, Fd, and Fc.

Among the immunoglobulin fragments, Fab contains the variable regions of the light chain and the heavy chain, the constant region of the light chain, and the first constant region (CH1) of the heavy chain, and has a single antigen-binding site. The Fab' fragments differ from the Fab fragments in terms of having the hinge region containing one or more cysteine residues at the C-terminus of the heavy chain $C_H1$ domain. The F(ab')2 fragments are produced as a pair of Fab' fragments by disulfide bonding formed between cysteine residues of the hinge regions of the Fab' fragments. Fv is the minimum antibody fragment that contains only the heavy-chain variable region and the light-chain variable region. The scFv (single-chain Fv) fragments comprise the heavy-chain variable region and the light-chain variable region that are linked to each other by a peptide linker and thus are present in a single polypeptide chain. Also, the Fd fragments comprise only the variable region and $C_H1$ domain of the heavy chain. These functional fragments of immunoglobulin molecules can be obtained using proteolytic enzymes (for example, a whole antibody is digested into Fab by digestion with papain and into F(ab')2 by digestion with pepsin) or through genetic recombination technology.

As used herein, the term "immunoglobulin Fc fragment" refers to an immunoglobulin fragment that is composed of two heavy chains that contribute two constant domains (CH2 and CH3), devoid of the variable domains of light and heavy chains, the constant domain 1 of the heavy chain (CH1) and the constant domain of the light chain (CL1). Optionally, the immunoglobulin Fc fragment may further comprise a hinge region attached to the constant domain of the heavy chain. Since it is a biodegradable polypeptide that can be metabolized in vivo, an immunoglobulin Fc fragment is safe for use as a drug carrier. In addition, an immunoglobulin Fc fragment is advantageous over a whole immunoglobulin molecule in terms of the preparation, purification and yield of a conjugate because of its lower molecular weight. Free of the Fab fragment, which is heterogeneous because it differs in amino acid sequence from one antibody to another, the immunoglobulin Fc fragment is expected to greatly increase the homogeneity of the conjugate while decreasing the likelihood of provoking the blood antigenicity of the conjugate.

The immunoglobulin Fc fragment of the present invention may be an extended Fc fragment which comprises a part of or the entirety of the constant domain 1 of the heavy chain (CH1) and/or the constant domain 1 of the light chain (CL1) devoid of the variable regions of the heavy and the light chains, so long as it shows effects substantially identical or superior to those of the classical Fc fragment. Further, the immunoglobulin Fc fragment of the present invention may be comprised of CH2 and/or CH3 that lacks a significant part of the amino acid sequence. Consequently, the immunoglobulin Fc fragment of the present invention may be composed of 1) CH1 domain, CH2 domain, CH3 domain and CH4 domain, 2) CH1 domain and CH2 domain, 3) CH1 domain and CH3 domain, 4) CH2 domain and CH3 domain, 5) a combination of one or more constant domains and an immunoglobulin hinge region (or a partial hinge region), or 6) a dimer of each constant domain of the heavy chain and the constant domain of the light chain.

In addition, the immunoglobulin Fc fragment of the present invention is intended to cover not only native amino acid sequences but also mutants thereof. The amino acid sequence mutant means an amino acid sequence different from the native sequence by deletion, insertion, non-conservative or conservative substitution of one or more amino acid residues or combinations thereof. For example, the amino acid residues at positions 214 to 238, 297 to 299, 318 to 322, or 327 to 331 of IgG Fc, which are known to play an important role in antibody binding, may be modified so as to be used as suitable binding sites. In addition, various mutants which, for example, lack a residue forming a disulfide bond or several N-terminal amino acids of the native Fc, or have an additional methionine residue at the N terminus of the native Fc are possible. Further, effector functions may be eliminated by removing a complement binding motif, e.g., C1q binding motif, or an ADCC (antibody-dependent cell mediated cytotoxicity) motif. Reference may be made to PCT Publication Nos. 97/34631 and 96/32478 concerning the preparation of amino acid sequence mutants of immunoglobulin Fc fragments. The Fc fragment may be a native form isolated from humans and other animals including cows, goats, pigs, mice, rabbits, hamsters, rats and guinea pigs, or may be a recombinant or a derivative thereof, obtained from transformed animal cells or microorganisms. In the former case, whole immunoglobulin is isolated from humans or animals, followed by enzymatic treatment. When treated with papain, the whole immunoglobulin is divided into Fab and Fc. Pepsin cleaves whole immunoglobulin into pF'c and F(ab). From these fragments, Fc or pF'c can be separated using size-exclusion chromatography. Preferred is a recombinant immunoglobulin Fc domain derived from the human Fc domain in microorganisms.

For the purposes of the present invention, the immunoglobulin Fc fragment may be one derived from IgG, such as an IgG1 Fc fragment, an IgG2 Fc fragment, an IgG3 Fc fragment, an IgG4 Fc fragment and the like, preferably an IgG2 Fc fragment or an IgG4 Fc fragment, more preferably an IgG4 Fc fragment, and most preferably an IgG4 Fc fragment encoded by the nucleotide sequence represented by SEQ ID NO: 1 or SEQ ID NO: 2, or an IgG4 Fc fragment comprising the amino acid sequence represented by SEQ ID NO: 10 or SEQ ID NO: 11.

The immunoglobulin Fc fragment may undergo an amino acid substitution which does not alter the activity of native proteins or peptides as a whole. Most typical substitutions occur between Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. As needed, the amino acids may be modified by, for example, phosphorylation, sulfation, acrylation, glycosylation, methylation, farnesylation, acetylation, amidation, etc. These modification methods are known in the art (H. Neurath, R. L. Hill, The Proteins, Academic Press, New York, 1979).

As used herein, the term "transformation" or "modification" refers to the genetic alteration of host cells (inclusive of prokaryotes, eukaryotes, animal cells and plant cells) resulting from the introduction of exogenous genetic material, whether carried by a plasmid or not, using a genetic manipulation technique. The term "transformant" means a cell which stably retains and expresses an exogenous genetic material introduced from the outside, whether carried by a plasmid or not, even though the cell divides many times. Any process by which a nucleic acid material can be introduced into an organism, a cell, a tissue, an organ, or a nucleic acid material may be employed to carry out transformation in the present invention. Preferably, standard methods known in the art may be selected according to host cells. Transformation into yeast hosts may be typically performed using a method described by Van Solingen (J. Bact., 1977, 130:946) and Hsiao et al. (Proc. Natl. Acad. Sci. (USA), 1979, 76:3829). Methods of transforming yeasts include, but are not limited to, electroporation using an electric device, and spheroplasting using a spheroplast devoid of cell walls. For the purposes of the present invention, the transformant may be in the form of a multi-copy clone resulting from the incorporation of an immunoglobulin G Fc gene to the genome of the yeast host. For the purposes of the present invention, no particular limitations are imparted to the transformant so long as it harbors an expression vector which comprises a polynucleotide encoding for a human immunoglobulin Fc fragment. By way of example, Pichia (Komagataella) pastoris HMC041 (Accession No. KCCM11348P) which has the expression vector pPIC9K-IgG4Fc comprising an immunoglobulin Fc fragment-encoding polynucleotide, or Pichia (Komagataella) pastoris HMC042 (Accession No. KCCM11350P) which has the expression vector pPIC9K-mPSCFc comprising an immunoglobulin Fc fragment-encoding polynucleotide may be used.

As used herein, the term "host cell" means a target cell to which an exogenous genetic material is introduced. Examples of the host cells useful in the present invention include, but are not limited to, yeasts (e.g., Pichia pastoris, Saccharomyces cerevisiae, Schizosaccharomyces sp., Neurospora crassa)). Preferably, yeasts are employed as host cells because they can express the recombinant immunoglobulin structurally similar to a native form, with neither N-terminal modification with an additional amino acid, nor the necessity of a refolding process, and can be safe against contamination with a matter of animal origin. More preferable are Pichia sp. yeasts, with most preference for Pichia pastoris.

The term "expression vector," as used herein, which describes a vector capable of expressing a target protein in a suitable host cell, refers to a genetic construct that comprises essential regulatory elements to which a gene insert is operably linked in such a manner as to be expressed in a host cell. No particular limitations are imparted to the expression vector if it carries a polynucleotide encoding for the immunoglobulin Fc fragment of the present invention. For the purposes of the present invention, the expression vector is configured to express an immunoglobulin Fc fragment after transformation into a *Pichia* sp. yeast. For example, it may be pPIC9K-IgG4Fc, represented by the cleavage map of FIG. 1, or pPIC9K-mPSCFc, represented by the cleavage map of FIG. 2.

The term "operably linked," as used herein, refers to a functional linkage between a nucleic acid expression regulatory sequence and a nucleic acid sequence encoding for a target protein in such a manner as to allow general functions. The operable linkage to a recombinant vector may be prepared using a genetic recombinant technique well known in the art, and site-specific DNA cleavage and ligation may be carried out using enzymes generally known in the art.

According to one embodiment of the present invention, the expression vectors pPIC9K-IgG4Fc and pPIC9K-mPSCFc, each comprising an immunoglobulin Fc fragment-encoding polynucleotide, are constructed. The expression vectors pPIC9K-IgG4Fc and pPIC9K-mPSCFc were transformed into *Pichia pastoris* to prepare transformants which were designated "*Pichia (Komagataella) pastoris* HMC041" and "*Pichia (Komagataella) pastoris* HMC042", and deposited at the Korean Culture Center of Microorganisms (located at 361-221, Hongje-1 dong, Seodaemungu, Seoul) on Jan. 7, 2013, with Accession Nos. KCCM11348P and KCCM11350P, respectively.

The term "multi-copy clone," as used herein, refers to a transformant in which multiple copies of an exogenous gene are randomly incorporated to the genome of the host cell by recombination or rearrangement upon the crossing of the exogenous gene with a certain genomic gene or site of the host cell after the introduction of the exogenous gene to the host cell by genetic manipulation. On the whole, the multi-copy clone may be a transformant in which one or more copies of a gene selectable by a Geneticin marker are inserted to the genome of the host cells, and preferably in which five or more copies of a gene selectable by a Geneticin marker of 3 mg/ml or higher are inserted to the genome.

In accordance with another aspect thereof, the present invention addresses a method for preparing an immunoglobulin Fc fragment, comprising culturing the transformant; and recovering the immunoglobulin Fc fragment from the culture. And the method might be characterized by no requiring an additional protein refolding process.

The recombinant *Pichia pastoris* yeast may be cultured in a suitable medium under a proper condition known in the art. The culturing process may be readily adjusted by those skilled in the art depending on the strain used.

The immunoglobulin Fc fragment recovered from the culture may be used without further purification, or purified using dialysis, salting-out, and chromatography. Of them, chromatography is the most widely used. There are no rules that can be universally applied irrespective of the kind and order of the columns employed. According to the features of the target proteins of the antibody, and the culturing process, selection may be made from among ion exchange chromatography, size exclusion chromatography, affinity chromatography, hydrophobic chromatography, and protein-A affinity column.

In accordance with a further aspect thereof, the present invention addresses an immunoglobulin Fc fragment, prepared by the method, for use as a drug carrier. Serving as a carrier, the immunoglobulin Fc fragment forms a conjugate with a drug and can increase the bioavailability of the drug.

As used herein, the term "drug" indicates a substance that exerts a therapeutic effect on humans or animals when administered thereto. As non-limitative examples, peptides, polypeptides, compounds, extracts, and nucleic acids fall within the scope of the drug, with preference for peptides or polypeptides.

As used herein, the term "carrier" refers to a substance that is linked to a drug, with the aim of minimizing a decrease in the physiological activity of the drug and increasing the in vivo stability of the drug. That is, the present invention provides many possible IgG1, IgG2, IgG3 and IgG4 Fc fragments for increasing in vivo sustainability of the drug and minimizing a decrease in the in vivo activity of the drug. Preferably, IgG2 Fc and IgG4 Fc fragments are provided. More preferably, the present invention provides an IgG4 Fc fragment. However, so long as it has an FcRn receptor-binding site necessary for in vivo sustainability, any Fc fragment may fall within the scope of the present invention.

The immunoglobulin Fc fragment prepared using the method of the present invention enjoys the advantage of requiring no additional refolding processes and being free of additional amino acid restudies at the N-terminus. Also, it can be expressed at an increased level, with a minimal load of endotoxin or pathogens of animal origin, and can be purified using a simple process. Since it is a biodegradable polypeptide that can be metabolized in vivo, the immunoglobulin Fc fragment with such advantages can be used as a drug carrier. In addition, the immunoglobulin Fc fragment is advantageous over a whole immunoglobulin molecule in terms of the preparation, purification and yield of a conjugate because of its lower molecular weight. Free of the Fab fragment, which is of heterogeneity because it differs in amino acid sequence from one antibody to another, the immunoglobulin Fc fragment is expected to greatly increase the homogeneity of the conjugate while decreasing the likelihood of provoking the blood antigenicity of the conjugate.

Among the subclasses of IgG, IgG4 is the least prone to binding to a complement (C1q). Given lower affinity for the complement, the Fc fragment is less apt to mediate effector functions such as ADCC (antibody-dependent cell cytotoxicity) and CDC (complement-dependent cytotoxicity) and thus to provoke unnecessary immune responses in vivo. Affinity for C1q is lower in IgG2 and IgG4 Fc fragments than IgG1 Fc fragments, and the lowest in IgG4 Fc fragments. For use as a drug carrier, the Fc fragment conjugated to a drug preferably has to exhibit low effector functions such as ADCC and CDC. For the purposes of the present invention, hence, IgG2 Fc and IgG4 Fc fragments are useful, with higher preference for IgG4 Fc fragments. That is, the immunoglobulin Fc fragment useful as a drug carrier in accordance with the present invention may be an Fc fragment derived from human IgG4 Fc fragment or a derivative thereof lacking a part of the hinge, as represented by SEQ ID NO: 10 or SEQ ID NO: 11, which may have the same amino acid sequence as the protein produced by the *E. coli* transformant HM11201 (KCCM-10660P) disclosed in Korean Patent No. 10-824505.

MODE FOR INVENTION

A better understanding of the present invention may be obtained through the following examples which are set forth to illustrate, but are not to be construed as limiting the present invention.

Example 1

Construction of Expression Vector for Producing Immunoglobulin Fc Fragment in *Pichia pastoris*

A recombinant expression vector for expressing a human immunoglobulin Fc fragment in *Pichia pastoris* yeast was constructed to anchor a nucleotide sequence (SEQ ID NO: 1) encoding a human immunoglobulin Fc fragment composed of an IgG4 hinge region and IgG4 constant domains CH2 and CH3, as follows.

DNA of the human immunoglobulin Fc fragment was obtained by PCR, with the plasmid pBG4CH1-3 disclosed in Korean Patent No. 10-0725314 serving as a template. First, a forward primer (SEQ ID NO: 3) was designed to contain an SnaB I restriction site for fusion to an alpha factor secretion signal sequence while a reverse primer (SEQ ID NO: 4) was configured to have an EcoR I restriction site. A DNA encoding the immunoglobulin G4 Fc fragment was amplified by PCR using these primers. PCR was performed with 30 cycles of denaturing at 95° C. for 40 sec, annealing at 60° C. for 30 sec, and extending at 68° C. for 50 sec.

(SEQ ID NO: 3)
5'-GCTTACGTAGAGTCCAAATATGGTCCCCCATGCC-3'

(SEQ ID NO: 4)
5'-CCGGAATTCTCATTTACCCAGAGACAGGGAGAGG-3'

The immunoglobulin G4 Fc fragment DNA (ca. 700 bp) thus obtained was cloned into a pPIC9K vector (Invitrogen). To be in frame with an alpha factor secretion signal sequence, the PCR product of the immunoglobulin G4 Fc fragment was digested with the restriction enzymes SnaIB I and EcoR I, and then ligated in the presence of T4 ligase to a pPIC9K vector which was previously treated with the same restriction enzymes. The resulting recombinant expression vector contained the immunoglobulin G4 Fc gene immediately downstream of the alpha factor secretion signal sequence, but the SnB I recognition site represented by the forward primer was also left on the vector, so that the immunoglobulin G4 Fc fragment, if expressed from the vector, would have two undesired amino acid residues at the N-terminus. To delete the SnaB I recognition site inserted into the junction between the alpha factor secretion signal sequence and the immunoglobulin G4 Fc gene, site-directed mutagenesis was conducted using a pair of primers represented by SEQ ID NOS: 6 and 7, and the resulting expression vector was designated pPIC9K-IgG4Fc (FIG. 1).

(SEQ ID NO: 6)
5'-GAGAAAAGAGAGGCTGAAGCTGAGTCCAAATATGGTCCCCCA-3'

(SEQ ID NO: 7)
5'-TGGGGGACCATATTTGGACTCAGCTTCAGCCTCTCTTTTCTC-3'

FIG. 1 is a schematic view illustrating processes of constructing the recombinant expression vector pPIC9K-IgG4Fc. As can be seen in FIG. 1, the pPIC9K-IgG4Fc expression vector contains a DNA of SEQ ID NO: 1 under the control of 5' alcohol oxidase 1 (AOX1) gene promoter, and can be integrated to the genomic DNA of a host cell through the 3' alcohol oxidase 1 (AOX1) gene located downstream of the immunoglobulin G4 Fc gene.

Example 2

Construction of Expression Vector for Producing Immunoglobulin Fc Fragment Partially Devoid of Hinge in *Pichia pastoris*

An expression vector for expressing an immunoglobulin Fc fragment partially devoid of the hinge region in *Pichia pastoris* was constructed to anchor a nucleotide sequence (SEQ ID NO: 2) human immunoglobulin Fc fragment composed of a part of a hinge of IgG4, and constant domains CH2 and CH3 of IgG4, according to the same strategy as described in Example 1.

A DNA encoding the human immunoglobulin Fc fragment partially devoid of a hinge region was obtained by PCR, with the plasmid pBG4CH1-3 described in Korean Patent No. 10-0725314 serving as a template.

First, a forward primer (SEQ ID NO: 5) was designed to contain an SnaB I restriction site for fusion to an alpha factor secretion signal sequence while a reverse primer (SEQ ID NO: 4) was configured to have an EcoR I restriction site. A DNA encoding the immunoglobulin G4 Fc fragment was amplified by PCR using these primers. PCR was performed with 30 cycles of denaturing at 95° C. for 40 sec, annealing at 60° C. for 30 sec, and extending at 68° C. for 50 sec.

(SEQ ID NO: 5)
5'-GCTTACGTACCATCATGCCCAGCACCTGAGTTCC-3'

The immunoglobulin G4 Fc fragment DNA (ca. 680 bp) thus obtained was cloned into a pPIC9K vector (Invitrogen). To be in frame with an alpha factor secretion signal sequence, the PCR product of the immunoglobulin G4 Fc fragment was digested with the restriction enzymes SnaIB I and EcoR I, followed by ligation in the presence of T4 ligase to a pPIC9K vector which was previously treated with the same restriction enzymes. The resulting recombinant expression vector contained the immunoglobulin G4 Fc gene immediately downstream of the alpha factor secretion signal sequence, but the SnB I recognition site represented by the forward primer was also left on the vector, so that the immunoglobulin G4 Fc fragment, if expressed from the vector, would have undesired two amino acid residues at the N-terminus. To delete the SnaB I recognition site inserted into the junction between the alpha factor secretion signal sequence and the immunoglobulin G4 Fc gene, site-directed mutagenesis was conducted using a pair of primers represented by SEQ ID NOS: 8 and 9, and the resulting expression vector was designated pPIC9K-mPSCFc (FIG. 2).

(SEQ ID NO: 8)
5'-TCTCTCGAGAAAAGAGAGGCTGAAGCTCCATCATGCCCAGCACCTGAGTTCCTG-3'

(SEQ ID NO: 9)
5'-CAGGAACTCAGGTGCTGGGCATGATGGAGCTTCAGCCTCTCTTTTCTCGAGAGA-3'

Figure 2:
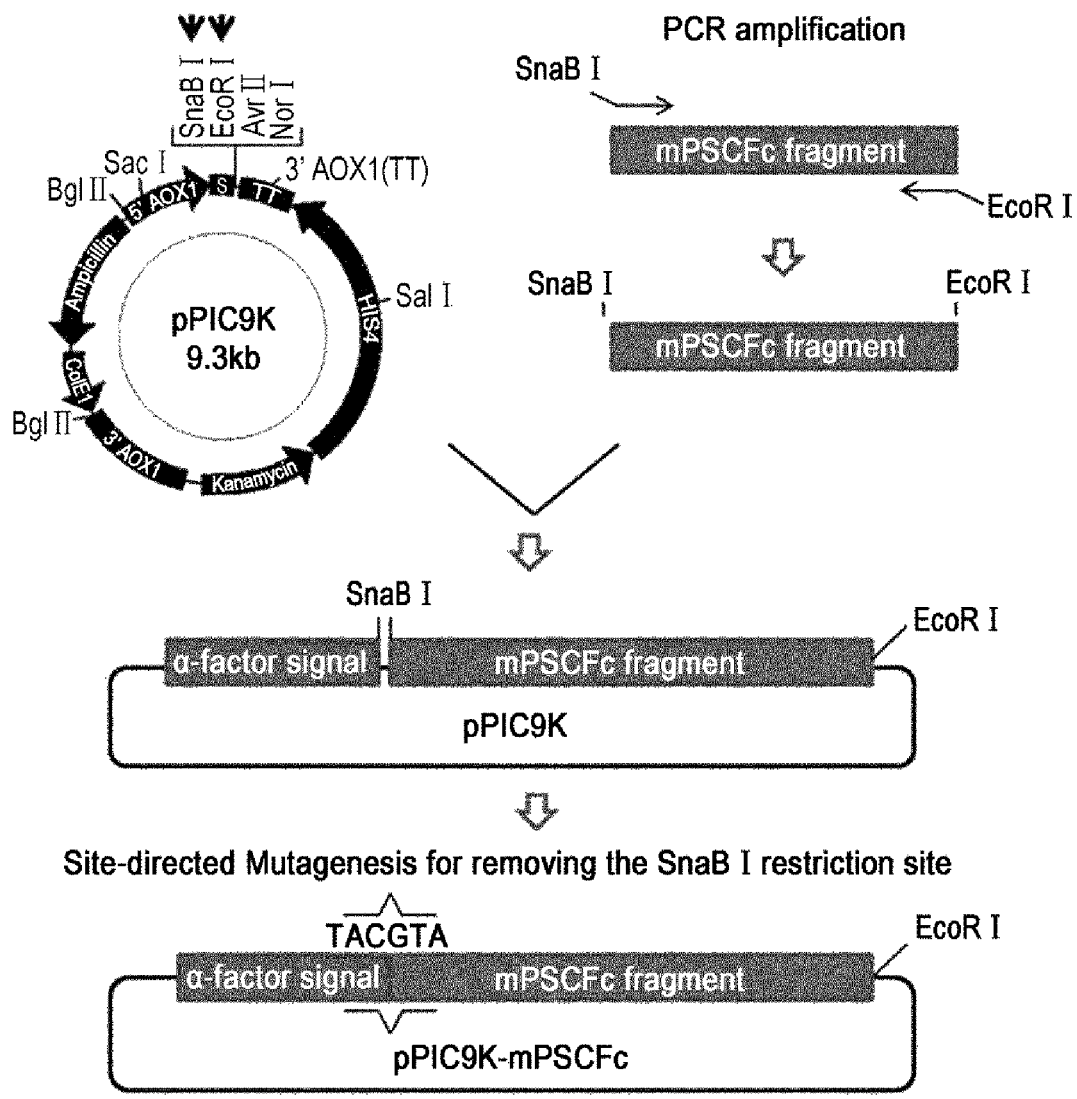
FIG. 2 is a schematic view illustrating processes of constructing the recombinant expression vector pPIC9K-mP-SCFc.

FIG. 2 is a schematic view illustrating processes of constructing the recombinant expression vector pPIC9K-mPSCFc. As can be seen in FIG. 2, the pPIC9K-mPSCFc expression vector contains a DNA of SEQ ID NO: 2 under the control of 5' alcohol oxidase 1 (AOX1) gene promoter, and can be integrated to the genomic DNA of a host cell through the 3' alcohol oxidase 1 (AOX1) gene located downstream of the immunoglobulin G4 Fc gene. The host cell transformed with the expression vector can secrete the immunoglobulin Fc fragment partially devoid of a hinge region to a culture medium, as driven by the alpha factor secretion signal sequence.

Example 3

Transformation to *Pichia pastoris* Yeast and Selection of Multi-Copy Clone

For use in stable transformation and integration to genomic DNA, the recombinant vectors pPIC9K-IgG4Fc and pPIC9K-mPSCFc, obtained respectively in Examples 1 and 2, were linearized by digestion with the restriction enzyme SalI. The linearized recombinant IgG Fc fragment expression vector was designed to be integrated into the genomic DNA of a host by recombination with the alcohol oxidase gene site of the host. Yeast *Pichia pastoris* KM71 and GS115 were used as hosts to be transformed with the recombinant expression vectors obtained in Examples 1 and 2. Transformation was carried out by electroporation, which is known to be the most popular and efficient for yeast. For use in transformation, spheroplasts of *Pichia pastoris* KM71 and GS115 were prepared according to the protocol provided by Invitrogen USA.

Figure 3:
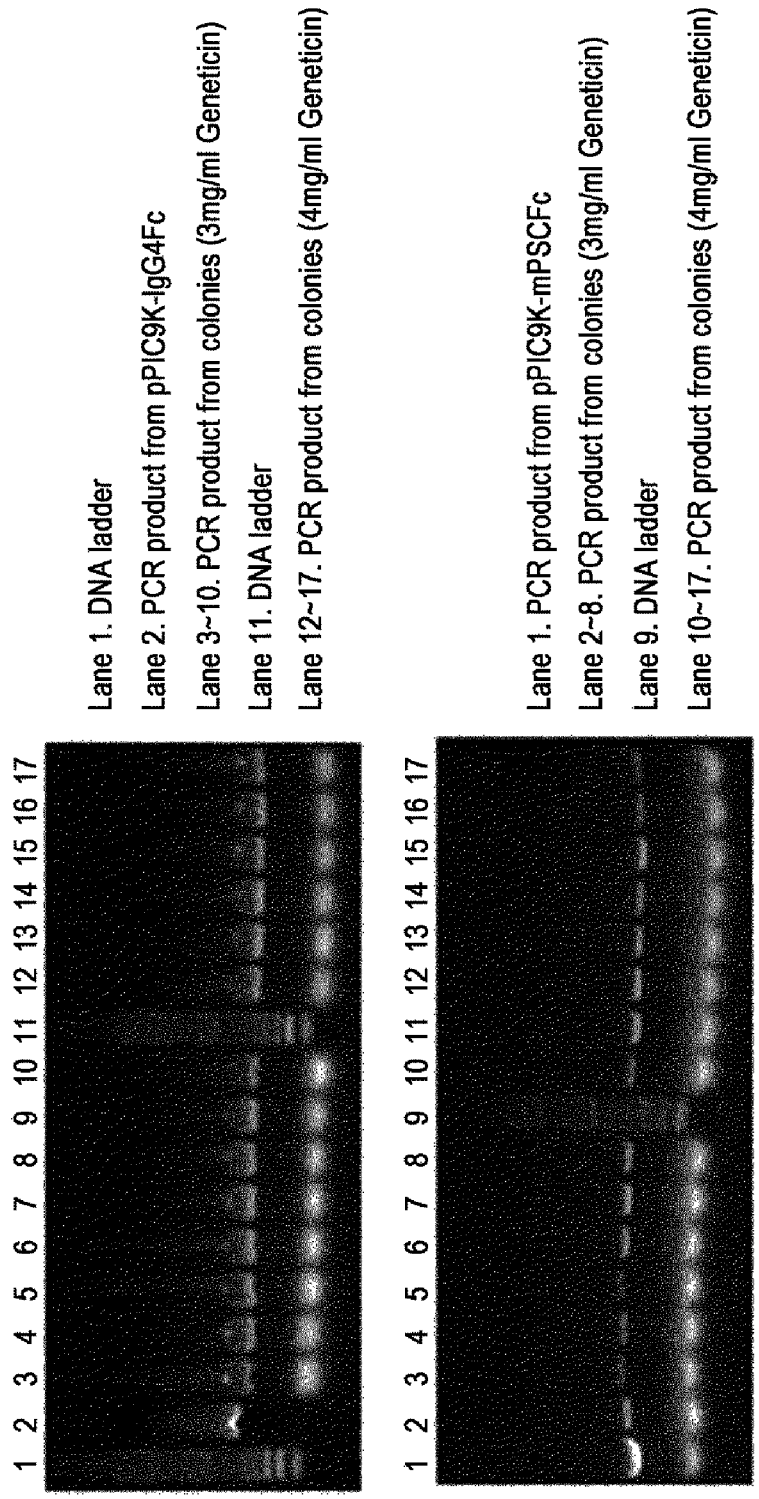
FIG. 3 is a PCR image showing the incorporation of genes of interest to the genomic DNA of multi-copy clones selected with 3 mg/ml and 4 mg/ml Geneticin.

After 10 ug of each of the linearized recombinant vectors was well mixed with 80 ul of the spheroplast of KM 71 or GS115, the mixture was incubated for 5 min in a 0.2 cm-gap-cuvette on ice. Then, an electric shock was applied to the cuvette at 2000V, 200 Ω, 25 uF in a Gene Pulser electroporation device (BIO-Rad) to induce transformation. The reaction mixture was added with 1 ml of chilled 1 M sorbitol, and spread over an MD (minimal dextrose) agar plate which was then incubated at 28° C. for 3 days to select His+ positive transformants. To discriminate multi-copy clones, each of the His+ positive transformants formed on the MD agar plate was homogeneously suspended in 1 ml of sterile distilled water and the suspensions were spread in an amount corresponding to $10^5$ cells over YPD agar plates containing various concentrations of Geneticin (0.5, 1.0, 2.0, 3.0, 4.0 mg/ml), followed by incubation at 28° C. for 5 days. Of the Geneticin-resistant, multi-copy clones thus selected, the colonies formed on the YPD agar plates containing 3.0 mg/ml and 4.0 mg/ml were subjected to colony PCR to examine whether the immunoglobulin fragment genes were incorporated to the genomic DNA. Briefly, PCR employed a pair of primers of SEQ ID NOS: 3 and 4 to examine the incorporation of the immunoglobulin Fc fragment gene, and a pair of primers of SEQ ID NOS: 5 and 4 to examine the incorporation of the gene encoding the immunoglobulin Fc fragment partially devoid of the hinge region. PCR was performed with 30 cycles of denaturing at 95° C. for 40 sec, annealing at 60° C. for 30 sec, and extending at 68° C. for 50 sec (FIG. 3). FIG. 3 is a PCR image showing the incorporation of the genes of interest to the genomic DNA of multi-copy clones selected with 3 mg/ml and 4 mg/ml Geneticin. As can be seen in FIG. 3, the PCR demonstrated the incorporation of the immunoglobulin Fc fragment genes to the genomes of host cells.

The transformants prepared by transforming *Pichia pastoris* strains with the expression vectors pPIC9K-IgG4Fc and pPIC9K-mPSCFc, which carried respective immunoglobulin Fc fragment genes, were designated "*Pichia (Komagataella) pastoris* HMC041" and "*Pichia (Komagataella) pastoris* HMC042", and deposited at the Korean Culture Center of Microorganisms (located at 361-221, Hongje-1 dong, Seodaemungu, Seoul) on Jan. 7, 2013, with Accession Nos. KCCM11348P and KCCM11350P, respectively.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A transformant, modified by introducing an expression vector comprising a polynucleotide encoding a human immunoglobulin Fc fragment into *Pichia* sp. Yeast, wherein the expression vector is pPIC9K-IgG4Fc having the cleavage map of FIG. 1, or pPIC9K-mPSCFc having the cleavage map of FIG. 2.

2. The transformant of claim 1, wherein the *Pichia* sp. yeast is *Pichia pastoris*.

3. The transformant of claim 1, wherein the immunoglobulin is IgG.

4. The transformant of claim 3, wherein the IgG is IgG1, IgG2, IgG3 or IgG4.

5. The transformant of claim 1, wherein the immunoglobulin Fc fragment comprises an amino acid sequence of SEQ ID NO: 10 or SEQ ID NO: 11.

6. A transformant, modified by introducing an expression vector comprising a polynucleotide encoding a human immunoglobulin Fc fragment into *Pichia* sp. yeast, wherein the polynucleotide comprises a nucleotide sequence of SEQ ID NO: 1 or SEQ ID NO: 2.

7. A transformant, modified by introducing an expression vector comprising a polynucleotide encoding a human immunoglobulin Fc fragment into *Pichia* sp. yeast, wherein the transformant is *Pichia* (*Komagataella*) *pastoris* HMC041 (Accession No. KCCM11348P) or *Pichia* (*Komagataella*) *pastoris* HMC042 (Accession No. KCCM11350P).

8. A method for producing an immunoglobulin Fc fragment, comprising:
   (a) culturing the transformant of claim 1; and
   (b) recovering the immunoglobulin Fc fragment from the culture.

9. The method of claim 8, wherein the method is characterized by no requiring an additional protein refolding process.

10. A method for producing an immunoglobulin Fc fragment, comprising:
    (a) culturing the transformant of claim 6; and
    (b) recovering the immunoglobulin Fc fragment from the culture.

11. The method of claim 10, wherein the method is characterized by no requiring an additional protein refolding process.

12. A method for producing an immunoglobulin Fc fragment, comprising:
    (a) culturing the transformant of claim 7; and
    (b) recovering the immunoglobulin Fc fragment from the culture.

13. The method of claim 12, wherein the method is characterized by no requiring an additional protein refolding process.

\* \* \* \* \*

SEQUENCE LISTING

<160> NUMBER OF SEQ ID NOS: 11

<210> SEQ ID NO 1
<211> LENGTH: 690
<212> TYPE: DNA
<213> ORGANISM: Homo sapiens
<220> FEATURE:
<223> OTHER INFORMATION: IgG Fc fragment sequence

<400> SEQUENCE: 1

```
gagtccaaat atggtccccc atgcccatca tgcccagcac ctgagttcct ggggggacca      60
tcagtcttcc tgttcccccc aaaacccaag gacaccctca tgatctcccg gacccctgag     120
gtcacatgcg tggtggtgga cgtgagccag gaagaccctg aggtccagtt caactggtac     180
gtggacggcg tggaggtgca taatgccaag acaaagccgc gggaggagca gttcaacagc     240
acgtaccgtg tggtcagcgt cctcaccgtc ctgcaccagg actggctgaa tggcaaggag     300
tacaagtgca aggtctccaa caaaggcctc ccatcctcca tcgagaaaac catctccaaa     360
gccaaagggc agccccgaga accacaggtg tacaccctgc ccccatccca ggaggagatg     420
accaagaacc aggtcagcct gacctgcctg gtcaaaggct tctatcccag cgacatcgcc     480
gtggagtggg agagcaatgg gcagccggag aacaactaca agaccacgcc tcccgtgctg     540
gactccgacg gctccttctt cctctacagc aggctaaccg tggacaagag caggtggcag     600 gagggggaacg tcttctcatg ctccgtgatg catgaggctc tgcacaacca ctacacgcag     660
aagagcctct ccctgtctct gggtaaatga                                      690
```

<210> SEQ ID NO 2
<211> LENGTH: 666
<212> TYPE: DNA
<213> ORGANISM: Homo sapiens

```
<220> FEATURE:
<223> OTHER INFORMATION: IgG Fc fragment sequence

<400> SEQUENCE: 2
ccatcatgcc cagcacctga gttcctgggg ggaccatcag tcttcctgtt cccccaaaa        60 cccaaggaca ccctcatgat ctcccggacc cctgaggtca catgcgtggt ggtggacgtg      120
agccaggaag accctgaggt ccagttcaac tggtacgtgg acggcgtgga ggtgcataat     180
gccaagacaa agccgcggga ggagcagttc aacagcacgt accgtgtggt cagcgtcctc     240
accgtcctgc accaggactg gctgaatggc aaggagtaca agtgcaaggt ctccaacaaa     300
ggcctcccat cctccatcga gaaaaccatc tccaaagcca agggcagcc ccgagaacca      360 caggtgtaca ccctgcccc atcccaggag gagatgacca agaaccaggt cagcctgacc      420
tgcctggtca aaggcttcta tcccagcgac atcgccgtgg agtgggagag caatgggcag     480
ccggagaaca actacaagac cacgcctccc gtgctggact ccgacggctc cttcttcctc     540
tacagcaggc taaccgtgga caagagcagg tggcaggagg gaacgtctt ctcatgctcc      600 gtgatgcatg aggctctgca caaccactac acgcagaaga gcctctccct gtctctgggt     660
aaatga                                                                666

<210> SEQ ID NO 3
<211> LENGTH: 34
<212> TYPE: DNA
<213> ORGANISM: Artificial Sequence
<220> FEATURE:
<223> OTHER INFORMATION: primer

<400> SEQUENCE: 3
gcttacgtag agtccaaata tggtccccca tgcc                                   34

<210> SEQ ID NO 4
<211> LENGTH: 34
<212> TYPE: DNA
<213> ORGANISM: Artificial Sequence
<220> FEATURE:
<223> OTHER INFORMATION: primer

<400> SEQUENCE: 4
ccggaattct catttaccca gagacaggga gagg                                   34

<210> SEQ ID NO 5
<211> LENGTH: 34
<212> TYPE: DNA
<213> ORGANISM: Artificial Sequence
<220> FEATURE:
<223> OTHER INFORMATION: primer

<400> SEQUENCE: 5
gcttacgtac catcatgccc agcacctgag ttcc                                   34

<210> SEQ ID NO 6
<211> LENGTH: 42
<212> TYPE: DNA
<213> ORGANISM: Artificial Sequence
<220> FEATURE:
<223> OTHER INFORMATION: primer

<400> SEQUENCE: 6
gagaaaagag aggctgaagc tgagtccaaa tatggtcccc ca                          42
```

<210> SEQ ID NO 7
<211> LENGTH: 42
<212> TYPE: DNA
<213> ORGANISM: Artificial Sequence
<220> FEATURE:
<223> OTHER INFORMATION: primer

<400> SEQUENCE: 7
tgggggacca tatttggact cagcttcagc ctctctttt tc                42

<210> SEQ ID NO 8
<211> LENGTH: 54
<212> TYPE: DNA
<213> ORGANISM: Artificial Sequence
<220> FEATURE:
<223> OTHER INFORMATION: primer

<400> SEQUENCE: 8
tctctcgaga aaagagaggc tgaagctcca tcatgcccag cacctgagtt cctg    54

<210> SEQ ID NO 9
<211> LENGTH: 54
<212> TYPE: DNA
<213> ORGANISM: Artificial Sequence
<220> FEATURE:
<223> OTHER INFORMATION: primer

<400> SEQUENCE: 9
caggaactca ggtgctgggc atgatggagc ttcagcctct cttttctcga gaga    54

<210> SEQ ID NO 10
<211> LENGTH: 229
<212> TYPE: PRT
<213> ORGANISM: Homo sapiens
<220> FEATURE:
<223> OTHER INFORMATION: IgG Fc fragment sequence

<400> SEQUENCE: 10

```
Glu Ser Lys Tyr Gly Pro Pro Cys Pro Ser Cys Pro Ala Pro Glu Phe
 1               5                  10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175
```

-continued

```
Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
            210                 215                 220

Leu Ser Leu Gly Lys
225

<210> SEQ ID NO 11
<211> LENGTH: 221
<212> TYPE: PRT
<213> ORGANISM: Homo sapiens
<220> FEATURE:
<223> OTHER INFORMATION: IgG Fc fragment sequence

<400> SEQUENCE: 11

Pro Ser Cys Pro Ala Pro Glu Phe Leu Gly Gly Pro Ser Val Phe Leu
  1               5                  10                  15

Phe Pro Pro Lys Pro Lys Asp Thr Leu Met Ile Ser Arg Thr Pro Glu
             20                  25                  30

Val Thr Cys Val Val Val Asp Val Ser Gln Glu Asp Pro Glu Val Gln
         35                  40                  45

Phe Asn Trp Tyr Val Asp Gly Val Glu Val His Asn Ala Lys Thr Lys
     50                  55                  60

Pro Arg Glu Glu Gln Phe Asn Ser Thr Tyr Arg Val Val Ser Val Leu
 65                  70                  75                  80

Thr Val Leu His Gln Asp Trp Leu Asn Gly Lys Glu Tyr Lys Cys Lys
                 85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
    210                 215                 220
```